United States Patent [19]

Rich

[11] Patent Number: 4,678,610

[45] Date of Patent: Jul. 7, 1987

[54] SILICONARYLOZIDES AND SILICONARYLISOCYANATES

[75] Inventor: Jonathan D. Rich, Ballston Lake, N.Y.

[73] Assignee: General Electric Company, Schenectady, N.Y.

[21] Appl. No.: 740,687

[22] Filed: Jun. 3, 1985

[51] Int. Cl.[4] .................. C07F 7/18; C07F 117/06
[52] U.S. Cl. ............................ 260/349; 528/21; 528/22; 556/414
[58] Field of Search ............... 556/414; 260/349

[56] References Cited

U.S. PATENT DOCUMENTS

| | | | |
|---|---|---|---|
| 2,340,757 | 2/1944 | Kaase et al. | 260/349 X |
| 3,347,919 | 10/1967 | Martin | 260/349 X |
| 3,466,314 | 9/1969 | Moedritzer et al. | 260/349 X |
| 3,494,951 | 2/1970 | Berger | 556/414 X |
| 3,584,024 | 6/9171 | Pepe | 260/398 X |
| 3,705,911 | 12/1972 | Thomson | 260/349 |
| 4,046,794 | 9/1977 | Pepe et al. | 556/414 X |
| 4,447,495 | 5/1984 | Engle, III | 260/349 X |

FOREIGN PATENT DOCUMENTS 374317  7/1973  U.S.S.R. .................. 556/414

OTHER PUBLICATIONS

Bonnet & Marechal, *Bulletin De La Societe Chimique De France*, 1972, No. 9, pp. 3561–3579.

*Primary Examiner*—Joseph Paul Brust
*Attorney, Agent, or Firm*—William A. Teoli; James C. Davis, Jr.; James Magee, Jr.

[57] ABSTRACT

A method is provided for making siliconarylacylazides by effecting reaction between an alkali metal azide and an organosilicon material such as an organosiloxane having chemically combined aroylacylhalide groups. Reaction products such as isocyanatoaryl terminated polydiorganosiloxane are also provided.

4 Claims, No Drawings

SILICONARYLOZIDES AND SILICONARYLISOCYANATES

CROSS REFERENCE TO RELATED APPLICATIONS

Reference is made to my copending application filed Mar. 29, 1985, Ser. No. 718,039, now U.S. Pat. No. 4,604,477, for Method for Making Silylaroylhalides and Reaction Products, assigned to the same assignee as the present invention and incorporated herein by reference.

BACKGROUND OF THE INVENTION

Prior to the present invention, as shown by Pepe, U.S. Pat. No. 3,584,024, certain isocyanato substituted siloxanes were made by the phosgenation of aminoorgano silane. Although the procedure of Pepe was useful in making particular isocyanate substituted organo polysiloxanes, it was found that the phosgenation of aminoorganosiloxane often resulted in the cleavage of the siloxane linkage and the production of unwanted chlorosilyl substituted orgnosiloxane. Bonnet et al., Bulletin Chemical Society of France 3561 (1972) also showed a similar reaction of aminophenyl substituted polydiorganosiloxanes with phosgene resulting in the production of the corresponding isocyanate.

Even though various prior art procedures have been found for making isocyanatoaryl substituted polydiorganosiloxanes, such procedures often have resulted in the production of undesirable side products, such as chlorosilyl substituted organosiloxanes, which have limited the utility of such isocyanato substituted organosilicon materials.

The present invention is based on my discovery that silicon arylacylazides which can be readily thermally decomposed to the corresponding silicon arylisocyanates, can be made by effecting reaction between an alkali metal azide or organometallic azide and an organo silicon material having at least one chemically combined group of the formula

where R is a $C_{(6-13)}$ divalent aromatic organic radical and X is a halogen radical, such as chloro, bromo or fluoro.

Organo silicon materials having chemically combined groups of formula (1) and a method for making such materials are shown in my copending application Ser. No. 718,039. For Example, an aromatic polyacylhalide, such as terephthaloyl chloride, is reacted with substantially an equivalent amount of a halopolysilane, such as 1,2-dichlorotetramethyldisilane, in the presence of a transition metal catalyst. There is obtained a p-halodiorganosilylbenzoyl halide as the exclusive silylaryl reaction product. Reaction of such p-halodiorganosilylaroylhalide can be used to make the corresponding disiloxane or polydiorganosiloxane having chemically combined units of formula (1).

STATEMENT OF THE INVENTION

There is provided by the present invention a method for making silicon arylacylazides comprising effecting reaction between an alkali metal azide or organometallic azide and an organosilicon material having at least one chemically combined group of formula (1).

In a further aspect of the present invention, there is provided a method for making organosilicon material having at least one chemically combined arylisocyanato group of the formula

where R is as previously defined, which comprises,
(1) effecting reaction between organosilicon material having at least one chemically combined arylacylhalide of formula (1), and an alkali metal azide, or organometallic azide to produce organosilicon material having at least one chemically combined arylacylazide group of the formula

and
(2) effecting the thermal decomposition of the resulting arylacylazide substituted organosilicon material.

Radicals which are included within R of formula (1) are for example, phenylene, tolylene, xylylene, naphthylene, anthrylene chlorophenylene, furanylene, thiophene, pyrrolene, etc. The unsatisfied valence bonds attached to siicon in formula 1 can be satified by C, H, O, or N atoms, or mixtures thereof, and preferably C or a mixture of C and O.

Azides which can be employed in the practice of the present invention are, for example, lithium azide, sodium azide, potassium azide, trimethylsilyl azide, etc.

Among the preferred organosiloxane having chemically combined groups of formula (1) which are useful in the practice of the invention are, for example, polydiorganosiloxne having the formula

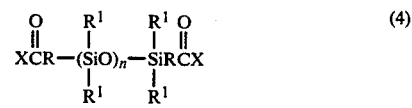

where R and X are as previously defined, n is a whole number equal to from 5 to 2000 inclusive, and $R^1$ is a member selected from the class consisting of monovalent $C_{(1-13)}$ hydrocarbon radicals and substituted $C_{(1-13)}$ monovalent hydrocarbon radicals. Radicals included within $R^1$ are preferably methyl or phenyl, a mixture of methyl and vinyl, a mixture of methyl and phenyl, a mixture of methyl and trifluoropropyl, and mixtures thereof.

The aromatic haloacyl-terminated polydiorganosiloxane of formula (4) can be made by effecting reaction between a silanol terminated polydiorganosiloxane having a value of n shown by formula (4), with a halosilylaroylhalide of the formula

where R, $R^1$ and X are as previously defined.

In accordance with the practice of the present invention, aromatic acyl halide terminated organosilicon material having at least one chemically combined group of formula (4), is contacted with an azide as previously defined at temperatures in the range of from 0° C. to 150° C. and in the presence of an organic solvent which is at least partially water miscible. Suitable organic solvents which can be used are, for example, acetone, tetrahydrofuran, dimethoxyethane, dioxane, diglyme and toluene. The resulting mixture can be agitated, such as stirred, for a period of from about 1 to 24 hours. The resulting silicon arylacylazide can then be recovered by a standard workup procedure such as the precipitation in an inert medium like water, followed by extraction, drying and removal of the extracting solvent under reduced pressure.

Siliconarylacylazide having chemically combined groups of formula (3), which are included within the scope of the present invention are, for example,

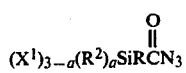

where R is as previously defined, $R^2$ is selected from $C_{(1-13)}$ monovalent hydrocarbon radicals and substituted $C_{(1-13)}$ monovalent hydrocarbon radicals and $X^1$ is selected from $R^2$ radicals, $R^2Q$ radicals, where Q O or S, and

radicals, where $R^3$ is selected from hydrogen, $R^1$ and a divalent organo radical, which can form part of a heterocyclic ring with $R^2$, and has a value of 0 to 3 inclusive.

Some of the siliconarylaacylazides are, for example, methoxydimethylsilylbenzoylazide, ethoxydimethylsilylbenzoylazide, phenoxydimethylsilylbenzoylazide, methylthiodimethylsilylbenzoylazide, phenylthiodimethylsilylbenzoylazide, trimethylsilylthiodimethylsilylbenzoylazide, N,N-dimethylaminodimethylsilylbenzoylazide, N,N-diethylaminodimethylsilylbenzoylazide, pyrollidine-N-dimethylsilylbenzoylazide.

In addition, there are included, silicon aryl acyl azide terminated polydiorganosiloxane of the formula

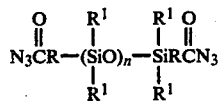

where R, $R^1$ and n are as previously defined.

The conversion of the silicon arylacylazide to arylisocyanate substituted organisilicon material can be achieved readily by thermal decomposition of the azide. A convenient procedure, for example, is by refluxing the organosilicon arylacylazide in an organic solvent, such as toluene, to expel nitrogen gas. Recovery of the desired arylisocyanato substituted organosiloxane can be readily achieved by stripping the organic solvent from the mixture.

The arylisocyanato terminated polydiorganosiloxane of the formula,

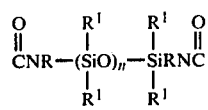

where R, $R^1$, and n are as previously defined, can have a viscosity in the range of from 500 centipoises to 40,000 centipoises.

Thus, the two formulas directly above, when $R^1$ is the preferred methyl and when R is phenylene, are

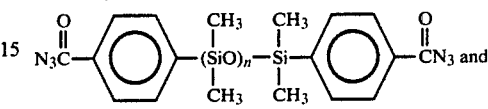

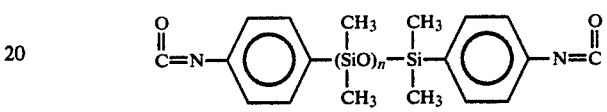

respectively, where n is previously defined.

The arylisocyanato terminated polydiorganosiloxane can be used to make silicone elastomeric adhesives when utilized in combination with organopolyamines or organic amines having other functional groups such as aminoorganoalkoxysilanes. There can be used at least one or more moles of amine, per mole of isocyanate for effective results. Some of the organic polyamines and organoamines having other reactive functional groups which can be used in combination with the arylisocyanate terminated polydiorganosiloxanes are, for example, ethylenediamine, propylenediamine, butylenediamine, hexamethylenediamine, bis(2-ethylamino)amine, tris(2-aminoethyl)amine, polyethyleneimine, γ-aminopropyltriethoxysilane, etc.

In order that those skilled in the art will be better able to practice the present invention, the following examples are given by way of illustration and not by way of limitation. All parts are by weight.

EXAMPLE 1

A solution of 2 grams (4.8 millimoles) of 1,2-bis(p-benzoylchloro)tetramethyldisiloxane in 25 ml. of dry acetone was cooled to 0° C. There was added dropwise to the solution, 0.65 grams (10 mm.) of sodium azide dissolved in 10 ml. of water. The mixture was then stirred for 1 hour. The solution was poured into 150 ml. of water and extracted three times with ml. portions of diethylether. The ether layers were combined and washed three times with water. The ether layer was then dried with magnesium sulfate and removed in vacuo. There was obtained 1.85 grams (91% isolated yield) of a pale-yellow oil. Based on method of preparation, the product was 1,3-bis(p-phenacylazido)tetramethyldisiloxane. Its identity was confirmed by its infrared spectrum.

EXAMPLE 2

A solution of 1.85 grams (4.4 millimoles) of 1,3-bis(p-phenylazido)tetramethyldisiloxane was refluxed in 50 ml. of dry toluene. Prior to reaching reflux temperature, expulsion of nitrogen gas from the solution was observed. After refluxing for 1 hour, gaseous evolution ceased and the mixture cooled to room temperature. There was obtained 1.32 grams (83% isolated yield) of pale-yellow oil upon removal of the solvent in vacuo. Based on method of preparation, the product was 1,3-bis(p-phenylisocyanato)tetramethyldisiloxane. Its identity was confirmed by its IR spectra, mass spec. calculated: $C_{18}H_{20}N_2O_3Si_2$ 368.1012; observed: 368.1007.

EXAMPLE 3

There was added at room temperature, a solution of 45 grams of a silanol terminated polydimethylsiloxane having an average of about 115 chemically combined dimethylsiloxy units dissolved in 150 ml of dry toluene to 40 grams of p-chlorodimethylsilylbenzoyl chloride. A constant vacuum of 20 torr was maintained to facilitate removal of HCl gas. Upon completion of the addition, a mixture which had been stirring, was stirred for an additional two hours to insure complete reaction. The toluene was then removed by evaporation from the mixture. There was obtained a two phase mixture consisting of a silicone fluid and excess chlorosilane. The chlorosilane was removed and the remaining material was heated to 120° C. at 0.1 torr.

There was added dropwise a 10 microliter solution of 0.18 gram of sodium azide to a solution of 5 gram of the above benzoyl chloride terminated polydimethylsiloxane fluid having an average of 165 chemically combined dimethylsiloxy units was prepared in 75 ml. of dry acetone. The entire mixture was stirred at room temperature for 1 hour. The mixture was then poured into 250 ml. of water and extracted with 3 ml. portions of water. The organic layer was separated and dried over anhydrous magnesium sulfate. It was heated in a rotary evaporator to remove the solvent. The remaining material was a clear silicone oil whose infrared spectrum was identical to the above-mentioned benzoyl terminated polydimethylsiloxane, except that there was an absence of carbonyl bands at 1780 and there was a presence of acylazide stretching frequencies and aromatic acylazide. The resulting oil was dissolved in 70 ml. of dry toluene and placed over an activated three angstrom molecular sieve for 18 hours. The solution was the decanted and heated to reflux temperature for hour. Upon cooling and removal of the solvent in vacuo, there was obtained 4.6 grams or a 90% yield of a clear silicone oil. Based on method of preparation, the product was a phenylisocyanato terminated polydimethylsiloxane having an average of about 165 chemically combined dimethylsiloxy units. Its identity was further confirmed by its infrared spectrum.

Three or four drops of bis(2-ethylamino)amine is rapidly mixed with one gram of the above phenyl isocyanate terminated fluid having a viscosity of approximately 3000 centipoise. The resulting mixture was applied as a thin film onto a 1"×3" glass plate. A similar plate was then applied onto the surface of the treated glass and allowed to rest for 5 minutes. There was obtained a glass composite having a tough transparent amide cross-linked silicone rubber adhesive which effectively bonded the glass plates together.

Two additional 1"×3" glass plates were surface treated with γ-aminopropyltrimethoxysilane and cured for 30 minutes at room temperature. The two treated plates were then further treated with a mixture of one gram of the phenyl isocyanato terminated polydimethysiloxane fluid which contained 3 to 4 drops of bis(2-ethylamino)amine. After 5 minutes a glass composite was obtained which exhibited improved adhesion over the glass composite made with glass plates without the δ-aminopropyltrimethoxysilane treatment.

Two additional glass plates were surface treated with δ-aminopropyltrimethoxysilane and cured for 30 minutes at room temperature. Treated glass plates were then further treated with a mixture of one gram of the phenylisocyanate terminated polydimethylsiloxane fluid, 100 milligrams of toluene diisocyanate and 50 milligrams of bis(2-ethylamino)amine. After the aforementioned ingredients were rapidly mixed together. A composite was obtained after 5 minutes of the two glass plates and a tough, opaque amide-cross-linked silicone rubber which was effective as an adhesive.

Although the above examples are directed to only a few of the very many variables which can be used in the practice of the present invention, it should be understood that the present invention is directed to those of a much broader variety of organisilicon material having chemically combined units of formula (1), alkali metal azides, and arylacylazide substituted and arylisocyanato substituted organo silicon materials obtained therefrom, as shown by the description preceding these examples.

What I claim as new and desire to secure by Letters Patent of the United States is:

1. Siliconarylazide having the formula,

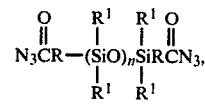

where R is a $C_{(6-13)}$ divalent arylene radical, $R^1$ is a $C_{(1-13)}$ monovalent hydrocarbon radical and n is an integer equal to 5 to 2000 inclusive.

2. Siliconarylisocyanate having the formula,

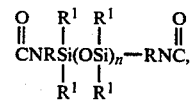

where R is a $C_{(6-13)}$ divalent aromatic arylene radical, $R^1$ is a $C_{(1-13)}$ monovalent hydrocarbon radical and n is an integer equal to 5 to about 2000 inclusive.

3. Phenylisocyanato-terminated polydimethylsiloxane having the formula,

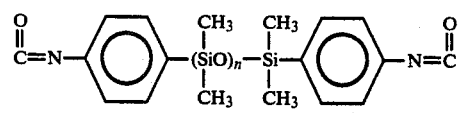

where n has a value of from 5 to 2000 inclusive.

4. Phenylazido-terminated polydimethylsiloxane having the formula,

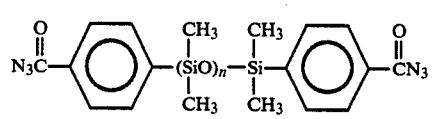

where n has a value of from 5 to 2000, inclusive.